United States Patent [19]

Babu et al.

[11] Patent Number: 4,720,455

[45] Date of Patent: Jan. 19, 1988

[54] PROGESTERONE ASSAY METHOD FOR MAMMALS AND MONOCLONAL ANTIBODY THEREFOR

[75] Inventors: Uma M. Babu, Voorhees, N.J.; Abdus S. Mia, Fairless Hills; Gregory D. Pancari, Gardenville, both of Pa.

[73] Assignee: Pitman-Moore, Inc., Terre Haute, Ind.

[21] Appl. No.: 773,398

[22] Filed: Sep. 6, 1985

[51] Int. Cl.[4] ............... G01N 33/53; C12N 15/00
[52] U.S. Cl. ................... 435/7; 435/172.2; 435/240.27; 435/810; 435/948; 435/548; 530/387; 530/808; 530/809; 935/89; 935/95; 935/102; 935/106; 935/110
[58] Field of Search ............ 435/7, 172.2, 240, 810, 435/948; 436/548; 530/387, 808, 809; 935/89, 95, 102, 106, 110

[56] References Cited

PUBLICATIONS

Maggio—Enzyme-Immunoassay (1980), CRC Press, p. 182.
Brochu et al—Chem. Abst., vol. 102(1985), p. 56, 231t.
Booman et al—Chem. Abst., vol. 101(1984), p. 204, 428j.
"Developement of a Direct Enzyme Immunoassay of Milk Progesterone and its Application to Pregnancy Diagnosis in Cows", Steroids, C. F. Chang and V. L. Estergreen, vol. 41, No. 2, Feb. 1983, pp. 173-195.
"Use of Microtitre Plate Eia for Direct Determination of Progesterone in Whole Milk: Application of Heterologous Systems for Improved Sensitivity", M. J. Sauer et al., Br. Vet. J. (1982), vol. 138, pp. 522-532.
"A High Performance, High Throughput Enzymeimmunoassay for the Analysis of Progesterone in Plasma or Milk", William F. Cleere, et al., Irish Vet. Journal 39: pp. 6-14, (1984).

Primary Examiner—Sam Rosen
Attorney, Agent, or Firm—Wendell R. Guffey; Thomas L. Farquer

[57] ABSTRACT

A progesterone concentration level test for mammalian body fluids particularly adapted for milk whereby estrus and pregnancy can be determined. The test can be carried out with a kit of several reagents, test tubes and a dip-stick carrying an anti-progesterone monoclonal antibody.

25 Claims, No Drawings

PROGESTERONE ASSAY METHOD FOR MAMMALS AND MONOCLONAL ANTIBODY THEREFOR

The present invention comprises a test method for the determination of levels of progesterone in the biological fluids of female mammals. In particular, the method is applicable to the determination of progesterone levels in the milk, serum or plasma of domestic mammals such as cows, mares and goats.

BACKGROUND OF THE INVENTION

The economic success of a commercial dairy operation is greatly influenced by the reproductive performance of the herd. For maximum profit and production, a cow should be pregnant by 90 days after calving, resulting in an average herd calving interval of 12.5 months. Less than optimum performance may be attributed to cows not cycling regularly, cows cycling but exhibiting poor signs of estrus and the stockman's failure to efficiently detect the cows in estrus. In some herds, 10 to 30% of cows in estrus escape detection and 10 to 25% of cows presented for insemination are not in estrus. Approximately 7% of pregnant cows may exhibit some signs of estrus. Insemination of such animals may cause termination of the existing pregnancy and wastage of the semen. Thus, accurate diagnosis of pregnancy, estrus and other related conditions is a valuable tool in animal management.

Progesterone is a steroidal hormone produced by the corpus luteum during the estrous cycle and pregnancy. Plasma progesterone levels accurately reflect different stages of the estrous cycle as well as the pregnancy status. Since progesterone levels in milk correlate well with those of plasma, milk progesterone tests have been extensively used to determine pregnancy, confirm estrus, diagnose reproductive disorders and monitor the effectiveness of infertility treatments in cows. Quantification of milk progesterone levels has been performed by radio immunoassay (RIA), a technique which requires expensive equipment and handling of hazardous radioactive materials. Another technique is the enzyme immunossay (EIA) wherein an enzyme bound to progesterone competes with the progesterone contained in the sample to be analyzed, the results being determined by using the enzyme to effect a color change proportional to the enzyme amount. Descriptions of such assays may be found in the following articles: W. F. Cleere et al. in the Irish Veterinary Journal, Vol. 39, pages 6–14 (1985); M. J. Sauer et at. in the British Vet. Journal, Vol. 138, pages 522–532 (1982); and C. F. Chang et al. in Steroids, Vol. 41, No. 2, pages 173-195 (1983).

However, even the most recent assay procedures described in the literature do not satisfy essential criteria to allow use of the test by technicians, usually dairymen, at the location of the cow, i.e., "cow-site", with test results available in a short period, e.g. less than 15 to 20 minutes. Of course any test which could be operated at cow-site, as opposed to a laboratory procedure, should also be accurate and indicative of a wide range of conditions in the cow, i.e., should convey as much information as possible and as accurately as possible. Another requirement of a test which would enable it to be a cow-site test is that the measurements which must be taken should not be so fine as to involve careful and meticulous physical operations. Thus, a practical cow-site test for progesterone would not involve manipulation of minute quantities, e.g. 10 to 50 microliters, of sample or reagent as is necessitated in prior assay procedures. It is thus an object of the present invention to provide an assay procedure for progesterone in a mammalian body fluid such as milk, serum or plasma which is accurate and indicative of a wide range of conditions, yet simple, fast and tolerant of differential amounts of reagents and samples used therein. That is, one or several microliters too much or too little reagent and/or sample should preferably have no discernible effect on the assay results.

SUMMARY OF THE INVENTION

An accurate, fast and sensitive test is provided for the assay of progesterone in a mammalian bodily fluid. The procedure has particular application for milk, serum or plasma and may be conducted in the relatively uncontrolled environment of the dairy barn, as opposed to other more delicate tests. The assay is a multiple tube procedure using a rod coated with a monoclonal antibody in which the solution of the final tube will be highly colored for a female in the follicular phase, e.g. a cow in estrus, and lightly colored for a female in the luteal phase, e.g. a pregnant cow. The assay reagents, pipettes and test tubes may be provided to the dairyman in the form of a kit.

DETAILED DESCRIPTION OF THE INVENTION

To test a mammalian bodily fluid such as serum, plasma or milk for progesterone, the invention comprises the steps of:
(I) immersing into a vessel holding a competitive solution comprising
  (a) a solution containing a known concentration of progesterone bound to an enzyme (the "Pe"), and
  (b) a known volume of said bodily fluid containing an unknown concentration of progesterone (the "P") to be assayed,
  a solid support carrying on the surface thereof and bound thereto, a monoclonal antibody to progesterone;
(II) removing said solid support from the competitive solution;
(III) immersing said solid support in a vessel holding an enzyme assay solution which comprises a chromogen which develops a color or shade upon exposure to the enzyme directly or through a substrate, said color or shade being proportional to the amount of enzyme; and
(IV) comparing the degree of coloration or shade in said enzyme assay solution to a standard.

Other progesterone assay methods using antibody binding techniques such as sandwich assays, can be used with the monoclonal antibody of the invention.

Throughout this specification, the term "solution" unless otherwise indicated, will be used to denote an aqueous liquid which may or may not be a true solution. It is known in the assay art that liquids to be tested need not be true solutions but rather may be fine emulsions or colloids provided, however, that the test reagents can interact with the material to be evaluated.

After step (II) and before step (III), there is preferably added step (II-i) which is the immersion of the solid support in a vessel holding a washing solution. Alternatively but less conveniently, the washing solution can simply be poured over the solid support.

The solid support used in the invention is a strip, rod, stick, cylinder or any other form which is sufficiently rigid to allow one to stir the solutions with it and place it in the vessels holding the solutions without it collapsing of its own weight. Preferably, the solid support is a short rod or "dip-stick" having the approximate dimensions of a pencil and formed of a liquid-impermeable and non-water-soluble plastic such as a polymer of styrene or vinyl chloride. A set of polymeric dip sticks may be molded by providing a backbone with about 10-20 sticks extending outwardly with a relatively thin piece of polymer between the backbone and each stick. When each stick is to be used, it is simply twisted back and forth to break it away from the backbone. A preferred dip stick is one suited to be used with standard commercial test tubes, e.g. tubes of 10×75 or 12×75 mm size. Thus, the dip stick may be about 90-100 mm long with a round shaft about 4-5 mm in diameter. Preferably, the dip stick has a 6-7 mm in diameter portion at one end (about 20 mm long) and a flat handle portion at the other end (about 10-15 mm long) of round or other shape. On one end of the dip stick, the monoclonal antibody will be coated leaving the other end for grasping during the operation of the test. So as to increase binding between the solid support and the monoclonal antibody, the support may be coated with a homopolymer of styrene or a copolymer of styrene and chloromethyl styrene, e.g. a styrene/chloromethylstyrene copolymer of a ratio of about 99/1 to 1/99, e.g. about 70/30. The polymer or copolymer may be dissolved in an organic solvent such as methylene chloride to make a solution having a polymeric weight concentration of about 0.5 to 8% by weight, e.g. about 1% by weight. The stick is dipped into the solution for a short period of time, e.g. about two seconds, and then air dried. The dip stick may be used singly or may be used as a set attached to each other via the backbone to allow multiple simultaneous testing by lining up the test tubes and immersing the entire dip stick assembly.

The monoclonal antibody may be applied to the solid support by direct or indirect means. Indirect bonding allows maximum exposure of the progesterone binding sites to the assay solution since the sites are not themselves used for binding to the support. Thus, the support can first be coated with an antibody, monoclonal or polyclonal, which is directed to the portion of the progesterone monoclonal which is not directed to progesterone. For example, if the monoclonal antibody for progesterone was derived by injecting progesterone or a complex thereof into a mouse, the initial coating of the support would be with an anti-mouse antibody derived from a goat or other mammal. Examples of such a first coating of antibody include Goat Anti-Mouse IgG (Fc specific) obtained from Cappel Laboratories of 1 Technology Court, Malvern, PA, U.S.A. 19355.

The monoclonal antibody for progesterone may be obtained by first conjugating the progesterone with a high molecular weight carrier to render the progesterone immunogenic. Carriers include immunoglobulins, keyhole limpet hemocyanin (KLH) and bovine serum albumin (BSA). The carrier is not believed to be a critical aspect of the invention although BSA was used to obtain Prog-431-135, the monoclonal antibody having the excellent properties described herein. The conjugate is then injected into a mammal, and the spleen or lymph nodes are removed and fused with a myeloma to obtain a hybridoma continuous cell line as known in the art. The hybridomas thus produced are screened to find those producing antibodies which are specific for progesterone, have little or no cross-reactivity with other steroids and yet bind quickly and firmly to progesterone. Basic references for this technique are the articles by Kohler and Milstein in Nature, Vol. 256, page 495 (1975) and by Milstein in Scientific American, page 66, (1980). U.S. Pat. No. 4,521,510 describes an immunoassay for theophylline which uses a monoclonal antibody, U.S. Pat. Nos. 4,361,549 and 4,529,700 also present a review of the technology and procedural details for monoclonal antibody production. Preferably, the progesterone monoclonal antibody used in the invention is an IgG type and is one which has affinity (strength of binding) and avidity (number of antigen molecules which bind per antibody molecule) characteristics such that a milk sample having a progesterone P concentration of about 8 nanograms per ml will result in an about ½ decrease in color intensity (when compared to a milk sample containing less than 0.5 nanograms/ml of progesterone) in the invention assay procedure where the number of binding sites on the stick is about equal to or slightly less than the number of Pe molecules presented to the stick in the competitive binding. With respect to cross reactivity, it is preferred that the monoclonal antibody have a cross-reactivity to corticosterone and estradiol-17-beta of less than 5% each, most preferably less than 3% each and even less than about 1% each.

In particular, the monoclonal antibody produced by the hybridoma continuous cell line Prog-431-135 deposited at the American Type Culture Collection 12301 Parklawn Drive, Rockville, Md., 20852 U.S.A. On Aug. 13, 1985 and given ATCC Accession Number HB 8886 can be used in the invention process. Such hybridoma and its monoclonal antibody are also part of the present invention. Such hybridomas may be maintained to continuously produce monoclonal antibodies as known in the art, e.g. by tissue culture or ascitic culture as described in "Selected Methods in Cellular Immunology", Ed. by B. B. Meshell et al. Chapter 17, W. H. Freeman 7 Co., San Francisco (1980) or by the Encapsel ™ process of Damon Biotech. Inc. of Needham Heights, Mass. 02194 described in U.S. Pat. Nos. 4,352,883; 4,386,895; 4,391,909 and 4,407,957.

The solution (a) in step (I) contains a known concentration of progesterone bound to the enzyme (Pe), e.g. a peroxidase enzyme, which will later be used to generate the color or shade. The concentration of Pe to be used will depend on the concentration of P in the particular bodily fluid chosen in the particular specie of mammal when that mammal is pregnant. Thus, a pregnant cow's milk will have a P concentration of about 8 to 50 nanograms/ml, e.g. typically about 8-15 ng/ml. The ratio of of P to Pe in solution (b) and (a) should be about 10 to 20. With the P value at 8 ng/ml and using 0.25 ml of the milk solution (b), it can be seen that the (a) solution should have a Pe concentration of about 0.2 ng/ml if 1.0 ml is used. Of course, when the cow is in estrus, the P concentration will decrease to or below the Pe concentration allowing the Pe to bind successfully and causing the color change in step (III). Examples of enzymes include alkaline phosphatase, beta-galactosidase or horseradish peroxidase. Many enzyme-chromogen or enzyme-substrate-chromogen combinations are known and used for enzyme-linked assays. The enzyme may be bound to the progesterone by a mixed anhydride reaction described by E. C. Dawson et al. in Steroids, Vol.

31, No. 3, pages 357-366 (1978) and by M. J. Saucer in Steroids, Vol. 38, No. 1, pages 45-53 (1981). The amount of solution (a) is not overly critical since it is the concentration and not the absolute amount of each of the two types of progesterone P and Pe which will determine the absolute amount of each which becomes bound to the monoclonal antibody coating.

An aspect of the present invention which results in significant advantages over prior assays conducted under laboratory conditions, is the amount of sample used. In the Cleere et al. assay described above, 200 microliter volumes of enzyme conjugate were used with 10 microliter volumes of standards, controls and unknown milk samples to result in a 20:1 volume ratio. Such small amounts of milk were used to minimize interference from other steroids and inhibitors present in the milk. Samplings on the order of 10 microliters are difficult to obtain physically, are subject to great percentage variations without extremely precise (and thus expensive) apparatus and require skilled handling. In contrast, the sensitivity and selectivity of the monoclonal antibody used in the invention as well as the indirect binding allow the invention assay to be operated with milk samples on the order of 0.25 ml, i.e., 250 microliters, and enzyme conjugate volumes on the order of 1.0 ml. i.e., 1000 microliters. The use of disposable and yet accurate pipettes for such volume is in part responsible for the invention process being more accurate and less expensive and time consuming than prior processes. In general, the volume ratio of solution (a):- solution (b) in the invention is less than about 10:1.

The washing step (II-i) for the solid support is carried out in a washing solution which may contain a detergent such as Tween-20, Tween-80 or sodium dodecyl sulfate. In prior assays a well is coated with an antibody for progesterone and several washings are required to prepare the well for the next stage, i.e., for chromogen and enzyme substrate introduction. In contrast, in the invention, only one such washing of the test rod is required.

In step (III), the test rod is immersed in the enzyme assay solution which determines the amount of enzyme coated on the rod and indirectly, the concentration of progesterone in the milk sample since the greater the concentration, the lower would have been the amount of enzyme-progesterone conjugate deposited. The enzyme assay solution contains a chromogen or substrate-chromogen combination specific for the enzyme used, i.e., a chemical system which develops or changes color or shade proportionally to the amount of enzyme present. Preferably, the enzyme assay solution is made up of hydrogen peroxide, which is broken down in direct proportion to the amount of various enzymes, and a chromogen which is transformed by the oxygen atom or radical released by the decomposition of hydrogen peroxide. Examples of such chromogens includes O-phenylenediamine,-2,2'-azinobis(3-ethylbenzthiazoline-sulfonic acid) ("ABTS") and 3,3',5,5'-tetramethylbenzidine and their derivatives such as water soluble derivatives including the dihydrochloride of 3,3',5,5'-tetramethylbenzidine. A suitable chromogen-substrate for an alkaline phosphatase is Sigma 104® phosphatase substrate (p-nitrophenyl phosphate) available from Sigma Chemical Co. of St. Louis, MO, U.S.A.

Simultaneously with steps (I)-(III), corresponding steps may be carried out with a known volume of the bodily fluid containing a known concentration of P in the place of fluid (b) and such a test can be the standard for step (IV). Other standards can either be a spectrophotometric reading of the assay solution compound to a predetermined value or a series of colorations or shades of varying intensity.

Although each of the steps I, (II-i) and (III) can be carried out in the same vessel, such as a test tube, if it is cleaned and washed after each of steps (I) and (II-i), a fast and convenient cow-site assay is best performed according to the invention by using three separate vessels for each of such steps. For example, a set of three test tubes labeled A, B and C may be used for each animal sample and control run using milk from an animal from outside the herd, e.g. from the manufacturer of the test kit.

The test kit of the invention for a bodily fluid from a female mammal will have the following components:
  a solution containing a known concentration of progesterone bound to an enzyme, e.g. a peroxidase enzyme;
  a washing solution;
  a solution of a chromogen which changes color or shade by the action of the enzyme directly or indirectly through action on a substrate, e.g. by the action of peroxidase on hydrogen peroxide;
  a volume of said bodily fluid containing a known concentration of progesterone, in particular from animals known to be in estrus and/or pregnant;
  pipettes for the transfer of said solutions;
  test tubes for said solutions; and
  a solid support, in particular adapted to be inserted into the test tubes, carrying on the surface thereof a monoclonal antibody to progesterone.

In the above test kit, the reagents may be supplied from storage bottles or one or more of the test tubes may be prefilled with the reagents or controls.

The following is a summary chart of the principal uses and procedures for such uses for the invention kit and method:

| | | | | SUMMARY OF INTERPRETATION | |
|---|---|---|---|---|---|
| Indication or use | No. of Samples | When | Type of Control | Result Color of Test vs Control | Diagnosis |
| a. Estrus Confirmation/ Non-Estrus | 1 | Day of Estrus | Estrus | Equal or Darker Lighter | estrus not in estrus |
| b. Pregnancy Status/ Non-Pregnancy | 1 | 20-23 Days | Pregnancy | Equal or Lighter Darker | pregnant not pregnant |
| c. Cyclicity | 3 | 7 Day Intervals | Estrus | Combination of Equal or Darker and Much Lighter All samples Equal or Darker | cycling non-cycling |
| d. Silent Estrus | 3-5 | On Alternate Days Starting 7 Days Before Expected Heat | Estrus | Lighter Followed by and Increase in Color to Similar or Darker | Will be in Heat 24-72 Hours After Sudden Increase |
| e. Fetal Death | 1 | 30, 40, 60 | Pregnancy | Darker | Fetal Death |

SUMMARY OF INTERPRETATION -continued

| Indication or use | No. of Samples | When | Type of Control | Result Color of Test vs Control | Diagnosis |
|---|---|---|---|---|---|
| | | & 80 days | | Equal or Lighter | Continued Pregnancy |
| f. Luteal Phase for Effective Use of Luteolytic Agents | 1-2 | Within 24 hours Before Treatment | Pregnancy | Equal or Lighter<br>Much Darker | In Luteal Phase<br>Not in Full Luteal Phase |
| | 1 | 72-90 hours after treatment | Estrus | Similar | Treatment Effective |
| g. Ovarian Disorders | 1 | Day of Palpation | Pregnancy | Equal or Lighter | Cystic or Persistent Corpus Luteum |
| | | | | Much Darker | Follicular Cyst or Malfunctional Ovary |
| h. Monitoring Infertility Treatment | 3 | 7 Day Intervals | Estrus | Combination of Equal or Darker and Much Lighter<br>All samples Equal or Darker | Initiation of Cycle<br>cycle not initiated |

Thus, the present invention comprises methods for progesterone assay, test kits for such assays, monoclonal antibodies which can be used in the assays, hybridomas to produce the monoclonal antibodies, progesterone assays utilizing the invention antibodies and surfaces which have such antibodies to be used for assays or purification of biological materials.

EXAMPLE 1

Preparation of Hybridoma a. Preparation of Progesterone Immunogen

Progesterone conjugated to bovine serum albumin (BSA) in the form of 11α-hydroxyprogesterone-hemisuccinate in the ratio of approximately 20 moles of steroid per mole of BSA was purchased from Sigma Chemicals Co. of St. Louis, Mo. 63178 U.S.A. One milligram of the progesterone-BSA conjugate was suspended in 1 ml of phosphate buffer saline (PBS) and then emulsified with an equal volume of either complete or incomplete Freund's adjuvant as explained below.

b. Immunization

Adult CAF$_1$ mice were injected with the immunogen of Example 1a intraperitoneally at the rate of 0.5 ml per animal every two weeks. The initial injection was the immunogen with Freund's complete adjuvant and the subsequent injections were with Freund's incomplete adjuvant. The animals were then tested for antibody titre by the ELISA test described below. Mice with high antibody titre (greater than 1:100,000) were selected for cell fusion. Three to four days before fusion, the mice were given intravenous injection of 0.25 mg of progesterone-BSA conjugate suspended in 0.5 ml of PBS.

c. Fusion to produce hybridoma

On the day of fusion, the animals were anesthetized, the spleens were removed aseptically and suspensions of single cells were made in 10 ml of Dulbecco's Media. The spleen cells were fused with non-secreting myeloma cells SP-2/0-Ag14 (which may be obtained from the American Type Culture Collection as ATCC CRL 1581) at a ratio of 5:1 using polyethylene glycol 1500 as the fusing agent. Approximately 200,000,000 spleen cells were mixed with 42,000,000 myeloma cells to which 1 ml of 50% polyethylene glycol was added and incubated for one min to effect fusion. The fused cells were washed in serum free medium by centrifugation, then resuspended in 50 ml of HAT media (diluted from 10× concentrated HAT). The cells were plated into 96 well microtitre plates at the rate of 0.2 ml ($10^6$ cells) per well and incubated in a 37° C. $CO_2$ incubator. Part of the media was replaced every third day and the wells were examined for growth of hybrid cells. A part of the supernatant from the wells showing hybrid cell growth as harvested and screened for antibody production by an ELISA test as described below.

d. Screening

Screening for antibody production was done by an ELISA test. Polyvinyl micro ELISA plates were coated with 11α-hydroxyprogesterone-BSA conjugate dissolved in carbonate bicarbonate buffer of pH=9.6. 50 microliters of different dilutions of sera or supernatant harvested from the wells with hybrid cell growth were incubated for 30 minutes in the washed, coated wells. After washing, 15 microliters of horseradish peroxidase linked goat anti-mouse IgG conjugate was incubated for 1 hour. After washing, 200 microliters of substrate solution consisting of hydrogen peroxide and ortho-phenylenediamine was added to each well. After 10 to 15 min of incubation, the reaction was stopped by adding 50 microliters of 5N $H_2SO_4$. Development of an amber color indicated antibody production against progesterone or BSA. The samples which indicated production of antibodies were further screened by an ELISA test using plates coated with BSA. The samples which gave positive results with the progesterone-BSA conjugate coated plates but negative results with BSA coated plates were considered positive for production of anti-progesterone antibodies. The hybrid cells producing anti-progesterone antibodies were expanded, subjected to limit dilution and screening to develop monoclonal antibody producing hybridoma cells.

Out of five separate fusions performed, 336 primary wells were found to produce anti-progesterone antibodies, 35 of which were subjected to limit dilution, subculturing for stability and antibody production to determine their usefulness for diagnostic purposes. Aliquots of cells were also viably frozen in liquid nitrogen for future use.

EXAMPLE 2

Preparation of Monoclonal Antibody

Limit-diluted stable hydridoma cells were expanded by growing in flasks. Approximately $1.5 \times 10^6$ hybridoma cells were injected intraperitoneally into pristane treated CAF$_1$ mice and ascitic fluid was harvested approximately 7 to 10 days after injection. Immunoglobulin IgG was purified from the ascitic fluid by ammonium sulfate precipitation and stored at below −60° C. for future use. The yield of purified IgG varied from 10 to 30 milligrams per milliliter of acitic fluid collected.

EXAMPLE 3

Performance Characteristics of Monoclonal Antibodies

Some performance characteristics of the purified monoclonal antibody of Example 2 produced by the hybridoma cells were studied by a competitive ELISA test using horseradish peroxidase (HRP) labeled progesterone. The peroxidase was conjugated to 11α-hydroxyprogesterone-hemisuccinate using the mixed anhydride reaction described by E. C. Dawson et al. in Steroids (supra). MicroELISA plates were coated with 0.1–0.2 ml/well of a solution containing an optimal amount (in the range of 5–10 micrograms/ml) of monoclonal antibody. The wells can be coated either directly or through goat anti-mouse IgG Fc fraction. A fixed amount of HRP labeled progesterone along with different amounts of progesterone ranging from 0–40 ng/ml were incubated in a well for 20 min. The unbound materials were removed by thorough washing after which color was developed using an $H_2O_2$ substrate with an ortho-phenylenediamine indicator. The reaction was stopped with $H_2SO_4$ and the absorbance was read and plotted against progesterone concentration to determine an inhibition curve. The clone designated Prog-431-135 showed a 40% drop in optical density with 8 nanograms/ml of progesterone and showed a fairly linear decrease in optical density values with increasing concentration of progesterone in milk over a wide physiologically important range, important with respect to the progesterone levels in cow's milk. On the basis of the above-mentioned performance data, clone Prog-431-135 was determined to have excellent assay characteristics. The cross-reactivity data for clone Prog-431-135 is shown in Table (I) below:

TABLE I

| Cross-reaction of some steriods with the Monoclonal Antibody Prog-431-135 | |
|---|---|
| Steroid | Cross-reaction* % |
| Corticosterone | 0.077% |
| Pregnenolone | 1.2% |
| Testosterone | 0.12% |
| Estradiol-17-beta | < <0.01% |
| 11-deoxycorticosterone | 0.32% |
| 17-alpha-hydroxy progesterone | 4.3% |
| 5-Beta-pregnan-3alpha 20alpha-diol | < <0.01% |
| Hydrocortisone | 0.003% |
| Estrone | 0.005% |

*Calculated as $\frac{\text{(amount of steroid needed for 50\% inhibition)}}{\text{(amount of progesterone needed for 50\% inhibition)}} \times 100$

EXAMPLE 4

Preparation of Coated Dipstick and Other Reagents

Dipstick

A polystyrene dip-stick was made by injection molding to form a pencil-shaped stick about 10 cm long and 7 mm in diameter. This design allowed easy and economic handling of the stick during the coating process and the individual dip stick provides greater surface area and ease of handling during the testing procedure. Although the polystyrene dip stick would, under suitable conditions, passively adsorb protein, such adsorption may be enhanced by first coating the dip stick with a styrene/chloromethylstyrene (S/CMS) polymer prior to protein adsorption. Thus, the polystyrene dip sticks were first coated with a thin layer of S/CMS by briefly (2–5 seconds) dipping the dip-sticks in a 1% solution of 70/30 S/CMS copolymer in methylene chloride followed by air drying. The coated dip sticks were then passively coated with 5 to 10 micrograms/ml of goat anti-mouse IgG (Fc fraction) antibody by dipping the stick up to 4–5 cm in the solution of the antibody in carbonate-bicarbonate buffer of pH=9.6 for up to 3 hrs at 37° C. or overnight at room temperature. After the incubation period, the sticks were washed thoroughly with a PBS-Tween washing solution to remove unbound antibody. Monoclonal anti-progesterone antibody was then immunologically bound to the thus-coated dip sticks by incubating the sticks in a solution of 25 to 35 nanograms/ml of monoclonal anti-progesterone antibody Prog-431-135 dissolved in PBS-Tween 20 solution containing 0.1% BSA. The incubation was carried for either 2–3 hrs at 37° C. or 6–8 hrs at room temperature. The unbound materials were removed by thorough washing in a PBS-Tween 20 solution and the sticks were stored in an aqueous storing solution of glycerol, PBS (phosphate buffered saline) and BSA in a ratio of 50 ml:50 ml:1 gm, respectively.

Enzyme Labeled Progesterone Reagent A 100 mg of horseradish peroxidase was conjugated to 3.0 mg of 11α-hydroxyprogesterone by the mixed anhydride method of Dawson et al. (supra). After exhaustive dialysis, the conjugate was diluted with a PBS-Tween 20 solution containing 4% BSA. The amount of dilution depends upon the extent of peroxidase-progesterone binding in any particular batch as known in the art. Thus, since 0.25 ml of conjugate-concentrate is added at the time of testing to 45 ml of the 4% BSA solution (to make Reagent A), the dilution to make the conjugate-concentrate is adjusted so as to result in a final Reagent A solution having about 0.1–0.2 nanograms/ml of progesterone. The progesterone-peroxidase conjugate concentrate is added to 4% BSA in PBS-Tween 20 as a diluent, results in reagent A as described below in Example 5.

Washing Solution Reagent B

The washing solution for the second row of test tubes was prepared by dissolving 2.85 gm of $Na_2HPO_4$, 0.2 gm of $KH_2PO_4$, 8 gm of NaCl and 0.75 ml of Tween 20 in 1 liter of distilled water.

$H_2O_2$ Substrate Reagent C

Reagent C was prepared by adding 3% $H_2O_2$ to 0.1M citrate buffer of pH 4.7 to a final concentration of 0.043% $H_2O_2$.

Substrate Chromogen Reagent D

The chromogen was prepared by dissolving 2.2 mg/ml of 3,3',5,5'-tetramethylbenzidine dihydrochloride in 1 ml of 0.1 Molar citrate buffer of pH 2.6.

Estrus Milk Control (Control E)

The estrus milk control was prepared by pooling the milk from three to five cows in standing estrus. The milk was then pasteurized for 15 mins and homogenized followed by adding potassium dichromate as a preservative to a final concentration of 0.05%.

Pregnancy Milk Control (Control P)

The pregnancy milk control was prepared by mixing Estrus milk control to milk obtained from three to five confirmed pregnant cows and treated similarly to the Estrus milk control. The mixing was carried out in a proportion to give a progesterone concentration of approximately 8–9 nanograms/ml which is the observed lower limit of progesterone concentration for milk from pregnant cows.

EXAMPLE 5

Test Kit and Procedure

An assay for progesterone in cow's milk was conducted using the reagents prepared in Example 4 as reagents A to D as well as Controls E and P. The kit contained the following components:

- Monoclonal antibody coated dip-stick—40 sticks
- Progesterone-peroxidase conjugate concentrate—0.5 ml
- Diluent for preparing progesterone-peroxidase conjugate (Reagent A)—45 ml
- Washing Solution (Reagent B)—90 ml
- Buffered Substrate (Reagent C)—45 ml
- Substrate Chromogen (Reagent D)—10.5 ml
- Estrus Milk Control (Control E)—5.5 ml
- Pregnancy Milk Control (Control P)—5.5 ml
- Pipeting syringe—1
- Pipeting tips—61 tips
- Rubber bulb droppers—3 droppers Other standard materials which are needed but may not be provided in the kit are the following:

- 12×75 mm test tubes
- Milk sample containers
- Milk sample preservative
- Test tube rack The reagents are removed from the storage box allowing them to come to room temperature for 10-15 minutes; additionally, the milk samples are allowed to come to room temperature. To avoid contamination, the procedure is started in the third row of a test tube rack. One test tube for each milk sample and milk control is placed in the third row of the rack. An Estrus Control is needed for confirmation or detection of estrus and the Pregnancy Milk Control is used for detection of pregnancy or the luteal phase. No more than ten tests including the controls should be run at one time for greater ease and convenience. The screw caps of the Reagent A, B and C bottles are replaced with the medicine droppers. The dip stick bag containing the dip sticks immersed in storing solution is opened.

Reagent A is prepared as follows. The Reagent A bottle is opened and 0.25 ml of the progesterone-peroxidase conjugate concentrate is added. The Reagent A bottle is closed and shaken with notation of the date of preparation of the reagent.

1 ml of Reagent A is added to each tube in the third row of the test tube rack. Each milk sample including the milk control is thoroughly mixed by gentle shaking to disperse the fat evenly and 0.25 ml of each milk sample including the control samples is added to the appropriate tube in the third row of the rack. Each test tube is labeled for the appropriate cow or control. A separate tip is used for the syringe for each milk sample and control.

A dip stick is removed from the storage bag and held by the flat end. The dip stick is shaken twice to remove excess adhering liquid and inserted bulb-end down into one of the tubes containing Reagent A and the milk sample. The appropriate number of sticks are then removed and inserted in the same manner with the remaining tubes in the third row of the test tube rack. The bulb end of the sticks should not be touched and equal time intervals should be used between each insertion of successive dip sticks. The tubes are then incubated for ten minutes at room temperature during which time another set of tubes in the second row is added to the rack. Into the second row of tubes is added 2 ml each of Reagent B. Finally, a third set of tubes is added in the first (front) row of the rack and 1 ml of Reagent C is added to each tube.

Using the pipeting syringe with a tip attached, 0.25 ml of Reagent D is added to each of the tubes in the first row containing Reagent C. At the end of the incubation period, the first dip stick inserted is taken out, shaken twice to remove excess adhering liquid and put into the corresponding second row tube containing Reagent B. Similarly, the other dip sticks are transferred in succession from the third row of tubes to the second row of tubes maintaining the same time intervals used between each removal and insertion. Each stick is moved up and down three times. The first dip stick is then removed from the second row of test tubes, shaken twice and put into the corresponding tube in the first row containing Reagents C and D. Thereafter, transfer of the remaining dip sticks is carried out successively maintaining the same time intervals as previously. The dip sticks are incubated until the milk control tube in the first row develops a blue color of the desired intensity:

| Control | Color |
|---------|-------|
| Estrus | Moderate Blue |
| Pregnancy | Pale Blue |

The color development should take five to ten minutes and is preferably carried out with both Control E and P, although, of course, only a single Control can be used. In addition, a color comparison chart can be used in place of the controls although actual controls will usually be a superior and more accurate comparison. Finally, the dip sticks are removed maintaining the same time intervals as previously described and the color of the solution in each of the test tubes are compared to the Controls.

For the test to be valid, the estrus milk Control E should produce a moderate blue color and the pregnancy milk Control P should produce a pale blue color. The intensity of the color developed in the test is inversely proportional to the concentration of progesterone in the milk. Therefore, test samples with high progesterone content produced a low degree of color while samples with low progesterone content produced a deeper color.

EXAMPLE 6

Efficacy of the Test in Detection and Confirmation of Estrus/Non-estrus and Pregnancy/Non-pregnancy in Cows The milk samples from cows suspected to be in estrus and from cows confirmed pregnant by rectal palpation were tested as in Example 5. The results are shown below in Table II.

TABLE II

| Status | No. of Samples Postive by Test Total No. of Samples Tested |
|--------|------------------------------------------------------------|
| confirmed pregnant | 221/225* |
| suspected of estrus | 137/149 |

*Two of the four animals tested negative returned to estrus within 7 to 10 days.
The 12 animals that were tested negative were found to have greater than 3 nanograms/ml progesterone concentration in the milk and did not conceive when inseminated on the day the test samples were taken.

EXAMPLE 7

Efficacy of the Test Using Body Fluids Other Than Milk and Milk from Animals Other Than Cows Serum and plasma from heifers and serum, plasma and milk from mares were tested as in Example 5 with appropriate Controls. The results showed that the test could visually identify the estrus/non-estrus and pregnancy/non-pregnancy status similar to that of cows.

What is claimed is:

1. A method of assaying progesterone in a bodily fluid derived from a female mammal which comprises the steps of:
    (I) immersing into a vessel holding a competitive solution comprising
        (a) a solution containing a known concentration of progesterone bound to an enzyme, and
        (b) a known volume of said bodily fluid containing an unknown concentration of progesterone to be assayed,
        a solid support carrying on the surface thereof and bound thereto, a monoclonal antibody to progesterone that is produced by the hybridoma continuous cell line designated by ATCC Accession Number HB 8886;
    (II) removing said solid support from the competitive solution;
    (III) immersing said solid support in a vessel holding an enzyme assay solution which comprises a chromogen or a substrate-chromogen combination which develops a color or shade upon exposure to said enzyme, said color or shade being proportional to the amount of enzyme; and
    (IV) comparing the degree of coloration or shade in said enzyme assay solution to a standard.
2. The method of claim 1, wherein said bodily fluid is milk.
3. The method of claim 1, wherein simultaneously with steps (I), (II) and (III), corresponding steps are carried out as a control with
    (c) a known volume of said bodily fluid containing a known concentration of progesterone
    in the place of bodily fluid (b).
4. The method of claim 3, wherein the degree of shade or coloration developed from the enzyme assay solution using fluid (c) is the standard for step (IV).
5. The method of claim 1, wherein said comparison step (IV) is conducted by obtaining a spectrophotometric reading of said assay solution and comparing the percent absorption or transmittance to standard predetermined values.
6. The method of claim 1, wherein said standard in step (IV) is a series of colorations or shades of varying intensity.
7. The method of claim 1, wherein said solid support comprises a polymer of styrene or vinyl chloride or a copolymer thereof.
8. The method of claim 1, wherein said solid support is a stick having said monoclonal antibody bound to one end portion thereof.
9. The method of claim 1, wherein said monoclonal anitbody is directly bound to said support.
10. The method of claim 1, wherein said monoclonal antibody is indirectly bound to said support through an antibody directed to the portion of the monoclonal antibody not specific for progesterone.
11. The method of claim 1, further comprising the step, after step (II) and before step (III), of:
    (II-i) immersing said solid support in a vessel holding a washing solution.
12. The method of claim 11, wherein said steps (I), (II-i) and (III) are each conducted in separate vessels.
13. The method of claim 11, wherein said step (II-i) is the only washing step between steps (II) and (III).
14. The method of claim 1, wherein said enzyme is a peroxidase enzyme and said substrate is hydrogen peroxide.
15. The method of claim 14, wherein said enzyme is alkaline phosphatase, beta-galactosidase or horseradish peroxidase.
16. The method of claim 1, wherein said chromogen is O-phenylenediamine,-2,2'-azinobis(3-ethylbenzthiazolinesulfonic acid) or 3,3',5,5'-tetramethylbenzidine or their derivatives.
17. The method of claim 1, wherein said peroxidase enzyme is horseradish peroxidase and said chromogen is 3,3',5,5'-tetramethylbenzidine dihydrochloride.
18. The method of claim 1, wherein the volume ratio of solution (a) to said bodily fluid (b) is less than about 10:1.
19. The hybridoma continuous cell line designated by ATCC Accession Number HB 8886.
20. The monoclonal antibody produced by the hybridoma continuous cell line designated by ATCC Accession Number HB 8886.
21. An immunossay for progesterone which utilizes the monoclonal antibody of claim 20.
22. A surface for the binding of progesterone molecules which comprises a substrate and bound directly or indirectly thereto, the monoclonal antibody of claim 20.
23. A test kit for the assay of the concentration of progesterone in a bodily fluid of a female mammal, which comprises:
    a solution containing a known concentration of progesterone bound to an enzyme;
    a washing solution;
    a solution of a chromogen which changes color or shade by the action of the enzyme;
    a volume of said bodily fluid containing a known concentration of progesterone;
    pipettes for the transfer of said solutions; and
    a solid support carrying on the surface thereof a monoclonal antibody to progesterone that is produced by the hybridoma continuous cell line designated by ATCC Accession Number HB 8886.
24. The test kit of claim 23, wherein said kit further comprises:
    a solution of hydrogen peroxide.
25. The test kit of claim 23, wherein said kit further comprises test tubes for said solutions.

* * * * *

UNITED STATES PATENT AND TRADEMARK OFFICE
CERTIFICATE OF CORRECTION

PATENT NO. : 4,720,455
DATED : January 19, 1988
INVENTOR(S) : Uma M. Babu et al

It is certified that error appears in the above-identified patent and that said Letters Patent is hereby corrected as shown below:

Column 1, line 51, "et at" should read --et al--

Column 5, line 1, "Saucer" should read --Sauer--

Columns 5 and 6, In the Table, d., column 5, "Lighter Followed by and Increase in Color to Similar or Darker" should read --Lighter Followed by an Increase in Color to Similar or Darker--

Column 14, Claim 9, line 2, "anitbody" should read --antibody--

Signed and Sealed this

Thirteenth Day of June, 1989

Attest:

DONALD J. QUIGG

*Attesting Officer*  *Commissioner of Patents and Trademarks*